United States Patent [19]

Fujii et al.

[11] Patent Number: 4,605,739
[45] Date of Patent: Aug. 12, 1986

[54] BENZOYL INDOLECARBOXYLATES

[75] Inventors: Setsuro Fujii, Toyonaka; Eizou Hattori, Sakado; Mitsuteru Hirata, Saitama; Hisashi Kunieda, Higashi-Murayama; Koichiro Watanabe, Niiza; Hiroshi Ishihama, Higashi-Murayama, all of Japan

[73] Assignee: Kowa Co., Ltd., Nagoya, Japan

[21] Appl. No.: 608,957

[22] Filed: May 10, 1984

[30] Foreign Application Priority Data

May 19, 1983 [JP] Japan .................. 58-87899

[51] Int. Cl.⁴ ............... C07D 403/12; A61K 31/495
[52] U.S. Cl. ........................................... 544/373
[58] Field of Search ................................. 544/373

[56] References Cited

U.S. PATENT DOCUMENTS 4,443,603  4/1984  Fujii et al. ............... 544/373

FOREIGN PATENT DOCUMENTS 0098713  1/1984  European Pat. Off. ......... 544/373

OTHER PUBLICATIONS

Derwent Abstract, 04863 E3, Kowa, Jp 81/158737.

Derwent Abstract, 35801 K, Kowa, Jp. 83/38243.

Primary Examiner—George F. Lesmes
Assistant Examiner—S. A. Gibson
Attorney, Agent, or Firm—Oblon, Fisher, Spivak, McClelland & Maier

[57] ABSTRACT

Benzoyl indolecarboxylates of the formula:

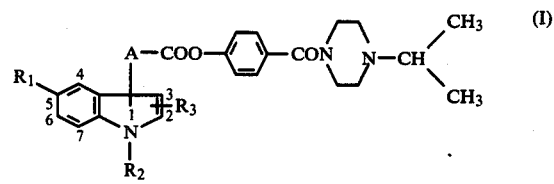

where $R^1$ is hydrogen, halogen, lower alkyl or lower alkoxy; $R^2$ is hydrogen, lower alkyl, acetyl or benzoyl; $R^3$ is hydrogen or lower alkyl; and A is a direct bond, or lower alkylene or vinylene substituted at the 2-, 3- or 5-position of the indole nucleus, are effective agents as chymotrypsin inhibitors.

9 Claims, No Drawings

BENZOYL INDOLECARBOXYLATES

BACKGROUND OF THE INVENTION

1. Field of the Invention

This invention relates to novel benzoyl indolecarboxylates.

More specifically, the invention relates to benzoyl indolecarboxylates represented by the following formula (I) and their acid addition salts:

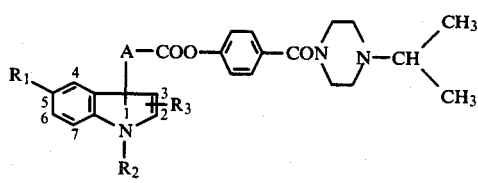

wherein $R_1$ is a hydrogen or halogen atom, or a lower alkoxy or lower alkoxy group;

$R_2$ is a hydrogen atom, or a lower alkyl, acetyl or benzoyl group;

$R_3$ is a hydrogen atom or a lower alkyl group; and

A is a direct bond, or a lower alkylene or vinylene group substituted at the 2-, 3- or 5-position of the indole nucleus.

2. Description of the Prior Art

The present inventors have previously found various benzoyl indolecarboxylates which can exert excellent chymotrypsin inhibitory characteristics, as disclosed in Japanese Patent Publication (Kokai) No. 38243/58 (1983).

Through continuous research efforts directed to the syntheses of a homologous series of compounds and to the determinations of their physiological activities, it has now been discovered that compounds of the formula (I) above and their acid addition salts have more specific inhibitory effects on chymotrypsin.

SUMMARY OF THE INVENTION

Compounds of the formula (I) and their acid addition salts are effectively useful as therapeutic agents in cases where a chymotrypsin inhibitory action is required. For example, these compounds may be used to treat or relieve pancreatic diseases.

Accordingly, this invention provides novel benzoyl indolecarboxylates of the formula (I) and their pharmaceutically acceptable acid addition salts.

DETAILED DESCRIPTION

Compounds of the formula (I) according to this invention can be produced, for example, by esterifying 4-substituted phenols of the following formula (II) and indolecarboxylic acids of the following formula (III). This reaction may be formulated as follows:

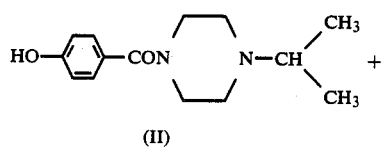

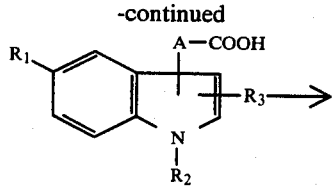

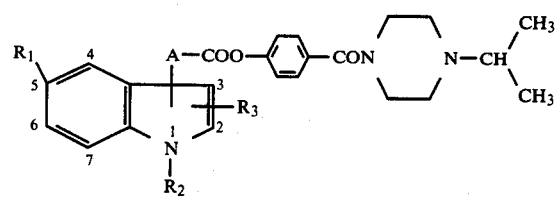

wherein the symbols $R_1$, $R_2$, $R_3$ and A are the same as defined hereinabove.

The esterification reaction under contemplation may be effected using conventional methods. One eligible method useful in the invention involves the reaction of reactive derivatives of the compounds of the formula (III), such as acid halogenides, acid anhydrides, mixed acid anhydrides, active esters, azides and the like, with the compounds of the formula (II). Another satisfactory method resides in allowing the compounds of the formula (II) to react with the compounds of the formula (III) in the presence of a dehydrating agent. Dicyclohexylcarbodiimide is a preferred example of such dehydrating agent.

The compounds of the formula (I) thus prepared, when found desirable, may be converted in known manner to their inorganic acid salts, such as hydrochlorides, sulfates, phosphates, hydrobromides and the like, or their organic acid salts, such as acetates, propionates, maleates, fumarates, tartrates, oxalates, citrates, methanesulfonates, benzenesulfonates, toluenesulfonates and the like.

Some selected compounds of this invention were tested with respect to their chymotrypsin inhibitory effects.

The tests were conducted in accordance with the procedure of Muramatsu et al [The Journal of Biochemistry, 62, 408 (1967)]. A mixture was prepared which was made up of 0.1 ml of a dimethylsulfoxide solution of each test compound, 0.1 ml of water and 0.1 ml of a buffer solution containing 10 μg/ml of chymotrypsin (0.1M Tris-HCl buffer, pH 8.0). The mixture was incubated for 10 minutes, followed by addition of 0.2 ml of a buffer solution containing 25 mM of an ethyl ester of acetyl-L-tyrosine. The resulting mixture was reacted at 37° C. for 30 minutes. The remaining substrate was caused to develop a color by the Hestrin method, whereupon its absorbance was measured at 530 nm. For comparative purposes, use was made of tosylphenylalanine chloromethyl ketone (TPCK) which is known as a good inhibitor for chymotrypsin.

The results are shown in Table 1.

TABLE 1

| Test Compound | Inhibitory Activity 50% Inhibitory Concentration (M) |
| --- | --- |
| 2 | $3 \times 10^{-7}$ |
| 3 | $4 \times 10^{-7}$ |

TABLE 1-continued

| Test Compound | Inhibitory Activity 50% Inhibitory Concentration (M) |
| --- | --- |
| 4 | 5 × 10⁻⁷ |
| 5 | 6 × 10⁻⁷ |
| 7 | 8 × 10⁻⁸ |
| 10 | 7 × 10⁻⁷ |
| 14 | 6 × 10⁻⁶ |
| Comparative compound (TPCK) | 5 × 10⁻⁴ |

Note:
The numbers of the test compounds are indicated as those of the corresponding examples given hereunder.

The following examples are provided to further illustrate this invention, but it should be noted that the invention is not limited thereto.

EXAMPLE 1

1-Isopropyl-4-[4-(1-acetyl-5-methoxy-2-methylindole-3-acetyloxy)benzoyl]piperazine To 30 ml of an ethyl acetate solution containing 2.61 g of 1-acetyl-5-methoxy-2-methylindole-3-acetic acid, 2.48 g of 1-(4-hydroxybenzoyl)-4-isopropylpiperazine and 0.12 g of 4-dimethylaminopyridine was added 2.27 g of dicychlohexylcarbodiimide. The reaction mixture was stirred at room temperature for 2 hours. Insoluble matter which had precipitated was removed by filtration, and the filtrate was extracted with 15 ml of 1N-hydrochloric acid. The extract was washed with ethyl acetate, neutralized with sodium hydrogencarbonate and then extracted with 30 ml of ethyl acetate. After being washed with water and dried, the ethyl acetate layer was concentrated under reduced pressure. The resulting crude crystals were recrystallized from ethyl acetate-petroleum ether to obtain 2.85 g (yield: 58.2%) of the title compound as colorless needle-like crystals having a melting point of 146° to 147° C.

EXAMPLE 2 TO 18

The procedure of Example 1 was repeated to obtain 17 compounds, their structural details and physical properties being tabulated in Table 2.

TABLE 2

| Example No. | Present Compound | | | | Salt | Yield (%) | Appearance | Melting Point (°C.) |
| --- | --- | --- | --- | --- | --- | --- | --- | --- |
| | R₁ | R₂ | R₃ | A | | | | |
| 2 | CH₃O | CH₃ | 2-CH₃ | 3-CH₂ | hydrochloric acid | 63.6 | colorless crystals | 223 226 (decomp) |
| 3 | CH₃O | H | 2-CH₃ | 3-CH₂ | " | 73.3 | pink crystals | 174 175 |
| 4 | CH₃ | H | 2-CH₃ | 3-CH₂ | oxalic acid | 41.6 | yellow needle crystals | 123 125 (decomp) |
| 5 | n-C₄H₉ | H | 2-CH₃ | 3-CH₂ | hydrochloric acid | 40.1 | " | 217 219 |
| 6 | — | H | H | 5- | " | 56.4 | colorless prism crystals | 154 156 |
| 7 | CH₃O | H | H | 3-CH₂ | oxalic acid | 67.9 | colorless crystals | 178 182 |
| 8 | CH₃O | C₆H₅C(O)— | 2-CH₃ | 3-CH₂ | hydrochloric acid | 71.8 | " | 220 225 |
| 9 | Br | H | H | 3-CH₂ | " | 68.5 | " | 139 140 |
| 10 | H | H | 2-CH₃ | 3-CH₂ | hydrochloric acid | 62.3 | light brown crystals | 222 223 (decomp) |
| 11 | H | H | H | 2- | — | 79.2 | colorless prism crystals | 179 180 |
| 12 | H | H | H | 3- | — | 6.4 | colorless crystals | 224 227 |
| 13 | H | H | H | 3-(CH₂)₃— | — | 75.6 | " | 101 104 |
| 14 | H | H | H | 3-CH₂ | — | 47.7 | light brown prism crystals | 145 147 |
| 15 | H | H | H | 3-(CH₂)₂— | — | 60.6 | colorless prism crystals | 129 130 |
| 16 | CH₃O | H | H | 2- | — | 70.2 | colorless needle crystals | 184 186 |
| 17 | H | H | H | 3-CH=CH— | — | 11.4 | yellow prism crystals | 229 230 |
| 18 | CH₃O | 4-Cl-C₆H₄C(O)— | 2-CH₃ | 3-CH₂— | methanesulfonic acid | 76.0 | light yellow needle crystals | 214 215 |

What is claimed is:

1. A benzoyl indolecarboxylate having the following formula or a pharmaceutically acceptable acid addition salt thereof:

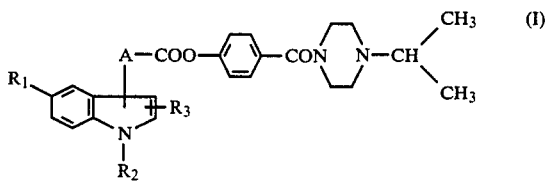

wherein
R¹ is a hydrogen or halogen atom, or a lower alkyl or lower alkoxy group;
R² is a hydrogen atom, or a lower alkyl, acetyl or benzoyl group;
R³ is a hydrogen atom or a lower alkyl group; and
A is a direct bond, or a lower alkylene or vinylene group substituted at the 2-, 3- or 5-position of the indole nucleus.

2. The benzoyl indolecarboxylate of claim 1, wherein R₁ is selected from the group consisting of hydrogen, bromine, methyl, methoxy and n-butyl; R₂ is selected from the group consisting of hydrogen, methyl, benzoyl and p-chloro benzoyl; R₃ is selected from the group consisting of hydrogen and 2-methyl; and A is selected from the group consisting of a direct bond, a 3-CH₂ group, a 3-CH=CH-group, a 3-(CH$_2$)$_3$ group and a 3-(CH$_2$)$_2$ group.

3. The compound 1-isopropyl-4-[4-(1-acetyl-5-methoxy-2-methylindole-3-acetyloxy)benzoyl]-piperazine.

4. The compound 1-isopropyl-4-[4-(1,2-dimethyl-5-methoxyindole-3-acetyloxy)benzoyl]-piperazine.

5. The compound 1-isopropyl-4-[4-(5-methoxy-2-methylindole-3-acetyloxy)benzoyl]-piperazine.

6. The compound 1-isopropyl-4-[4-(2,5-dimethylindole-3-acetyloxy)benzoyl]-piperazine.

7. The compound 1-isopropyl-4-[4-(5-n-butyl-2-methylindole-3-acetyloxy)benzoyl]-piperazine.

8. The compound 1-isopropyl-4-[4-(5-methoxyindole-3-acetyloxy)benzoyl]-piperazine.

9. The compound 1-isopropyl-4-[4-(2-methylindole-3-acetyloxy)benzoyl]-piperazine.

* * * * *